United States Patent
Sheverev et al.

(10) Patent No.: US 7,770,463 B2
(45) Date of Patent: Aug. 10, 2010

(54) SHEAR STRESS MEASUREMENT APPARATUS

(75) Inventors: Valery A. Sheverev, West Orange, NJ (US); Vadim Stepaniuk, Bloomfield, NJ (US)

(73) Assignee: Lenterra, Inc., West Orange, NJ (US)

( * ) Notice: Subject to any disclaimer, the term of this patent is extended or adjusted under 35 U.S.C. 154(b) by 48 days.

(21) Appl. No.: 12/313,922

(22) Filed: Nov. 26, 2008

(65) Prior Publication Data

US 2009/0133505 A1   May 28, 2009

Related U.S. Application Data

(60) Provisional application No. 60/990,352, filed on Nov. 27, 2007.

(51) Int. Cl.
*G01L 1/24* (2006.01)
(52) U.S. Cl. ............................................ 73/800; 73/760
(58) Field of Classification Search ............ 73/760–800
See application file for complete search history.

(56) References Cited

U.S. PATENT DOCUMENTS

| | | | |
|---|---|---|---|
| 4,464,928 A | 8/1984 | Dealy | |
| RE34,663 E * | 7/1994 | Seale | 600/587 |
| 5,438,879 A | 8/1995 | Reda | |
| 5,511,428 A * | 4/1996 | Goldberg et al. | 73/777 |
| 5,883,310 A | 3/1999 | Ho et al. | |
| 6,389,197 B1 | 5/2002 | Iltchenko et al. | |
| 6,426,796 B1 | 7/2002 | Pulliam et al. | |
| 2003/0118075 A1 | 6/2003 | Schweiger et al. | |
| 2006/0137467 A1* | 6/2006 | Horowitz et al. | 73/815 |
| 2008/0158542 A1* | 7/2008 | Otugen et al. | 356/35.5 |

OTHER PUBLICATIONS

Javad Shajii, et al., A Microfabricated Floating-Element Shear Stress Sensor Using Wafer-Bonding Technology, Journal of Microelectromechancial Systems, vol. 1, No. 2, (Jun. 1962), pp. 89-94.

Martin A. Schmidt, et al., Design and Calibration of a Microfabricated Floating Element Shear Stress Sensor, IEEE Transaction on Electron Devices, vol. 35, No. 6, (Jun. 1988), pp. 750-757.

(Continued)

*Primary Examiner*—Max Noori
(74) *Attorney, Agent, or Firm*—Barley Snyder LLC (57) ABSTRACT

A shear stress sensor for measuring the shear force of a fluid flowing along a wall. A floating member, flush with the wall, senses a shear force of the flowing fluid. The floating member is mounted by support means to a base element that is placed in the wall, so that the floating member is flush with the wall and a shear force, sensed by the floating member, is translated via the support means to a micro-resonator. The force acting on the micro-resonator changes the shape and the refractive index of the micro-resonator, thereby changing the resonant frequency of the micro-resonator and causing a shift in the spectrum of wavelengths of light that is introduced to the micro-resonator. This shift in the spectrum of wavelengths is representative of the shear force of the flowing fluid.

15 Claims, 9 Drawing Sheets

OTHER PUBLICATIONS

A. Padmanabhan, et al., Micromachined Sensors for Static and Dynamic Shear-Stress Measurements in Aerodynamic Flows, Transducers International Conference on Solid-State Sensors and Actuators, Chicago, Jun. 16-19, (1997), pp. 137-140.

Michael Kozhevnikov, et al., Optical Force Sensor Based On Whispering Gallery Mode Resonators, American Institute of Aeronautics and Astronautics, Polytechnic University, Brooklyn, NY 11201, pp. 1-10.

V.S. Ilchenko, et al., Strain-turnable High-Q Optical Microsphere Resonator, Optics Communications 145 (1998) pp. 86-90.

Jiang Zhe, et al., A Microfabricated Wall Shear-Stress Sensor With Capacitative Sensing, Journal of Microelectromechanical Systems, vol. 14, No. 1, (Feb. 2005), pp. 167-175.

Tal Carmon, et al. Wavelength-independent Coupler from Fiber To An On-Chip Cavity, Demonstrated Over An 850 nm Span, Optics Express, vol. 15, No. 12, (Jun. 11, 2007), pp. 77677-7681.

D. Fourguette, et al., An Optical MEMS-Based Shear Stress Sensor for High Reynolds Number Applications, American Institute of Aeronautics and Astronautics Inc., (2003), pp. 1-8.

* cited by examiner

SHEAR STRESS MEASUREMENT APPARATUS

CROSS REFERENCE TO RELATED APPLICATIONS

This application is a non-provisional application based on and claiming the priority of Provisional Application 60/990,352 filed Nov. 27, 2007.

FIELD OF THE INVENTION

The present invention relates, in general, to measuring wall shear stress (also known as "skin friction") in fluid flows and, in particular, to apparatus for measuring skin friction by determining the magnitude of a shift in an optical spectrum known as "whispering gallery modes" (WGM).

BACKGROUND OF THE INVENTION

The accurate measurement of wall shear stress remains a challenge in many industrial applications as well as in scientific research. Precise knowledge of shear stress can benefit many fields of human activity. For example, it can (a) reduce the cost of manufacturing and increase quality and throughput of certain products in the pharmaceutical, food, paint, and coating industries, and (b) improve the performance of aircraft. The real-time measurement of the local wall shear stress is important whenever dynamic flow control is required. Despite the long history of wall shear force measurement attempts using various approaches, the state of the art is still insufficient to meet all needs.

The ways of measuring shear stress fall into three categories: Indirect, Semi-Direct and Direct.

Most of the available sensors for measuring shear stress use indirect measurement techniques where the wall shear stress is inferred, through a set of assumptions, from another flow property, such as, for example, streamwise velocity or heat transfer rate, measured at or near the wall. These Indirect measurement methods include, for example:

hot-wire/film-based anemometry (U.S. Pat. No. 5,883,310)

laser-based near-wall flow velocity measurements (D. Fourguette, D. Modarress, D. Wilson, M. Koochesfahani, M. Gharib, "An Optical MEMS-based Shear Stress Sensor for High Reynolds Number Applications," AIAA-2003-742, 41st Aerospace Sciences Meeting and Exhibit, Reno, Nev., Jan. 6-9, 2003)

To retrieve information about shear stress, the indirect methods for measuring shear stress require precise modeling of the flow near the wall and knowledge of flow parameters such, as temperature and viscosity. For most applications, these models are not developed sufficiently well and the parameters are not well known. Laser-based flow velocity methods also require the fluid to be sufficiently transparent for the laser radiation, thus restricting the field of applications of these methods.

Another method, that can be classified as Semi-Direct and that has been frequently used in aerodynamic applications, is the surface oil-film/liquid-crystal interferometry (see, for example, U.S. Pat. No. 5,438,879). This approach, however, does not provide dynamic measurement of the wall shear stress and the spatial resolution can be poor. Technically, this approach requires covering an extended part of the wall with a film and having optical access to the film that can be difficult to implement in applications other than aerodynamic. Also, for high levels of shear stress the film may be susceptible to mechanical damage.

Direct wall shear measurement techniques are preferable because they measure a motion of a floating element, positioned flush within the wall, that is directly caused by the shear force (U.S. Pat. No. 4,464,928). In these methods, the measurement of the floating element displacement is measured that is accomplished by a number of techniques:

A. Electrical

Piezoresistive—In this approach, the shift of the floating element causes deformation of the piezoresistive element that is translated into electric signal (see, for example, J. Shajii, K-Y. Ng, M. Schmidt, "A Microfabricated Floating Element Shear Stress Sensor Using Wafer-Bonding Technology," Journal of Microelectromechanical Systems, V.1, No. 2, 1992, pp. 89-94)

Capacitor-based—In this approach, a floating element is mounted on one of the capacitor plates, so that the shift of the floating element changes the capacitance and this change is measured by electrical/electronic means (for example, M. Schmidt, R. Howe, S. Senturia, J. Artitonidis, "Design and Falibration of a Microfabricated Floating-Element Shear-Stress Sensor," IEEE Transactions on Electron Devices, v35, n6, 1988, pp. 750-757). These miniature electrical shear stress sensors, while showing satisfactory results in laboratory tests, to date have found limited applications due to following drawbacks:

(1) Small dynamic range of shear stress measurement
(2) Susceptibility to electromagnetic interference
(3) Low sensitivity for piezoresistive MEMS sensors
(4) For capacitance-based sensors, it is intrinsically difficult to separate shear stress from pressure (or from the force directed normal to the floating element surface)

B. Optical

Optical position measurement—In this approach, the floating element is illuminated from above and the shift is measured by an array of photodiodes placed below the element (A. Padmanabhan, M. Sheplak, K. S. Breuer and M. A. Schmidt, "Micromachined Sensors for Static and Dynamic Shear-Stress Measurements in Aerodynamic Flows," TRANSDUCERS '97, 1097 international Conference on Solid-state Sensors and Acfuators, Chicago, June 16-19, pp. 137-141, 1997).

The basic difficulty of this method is the requirement of flow to be transparent for the illuminating laser radiation that should be arranged externally. This method is similar in design to the oil film sensing described above.

Optical resonance methods—These methods rely on the deflection of an optical beam to convert any change in a mechanical attribute of a structure (for example, a displacement of the cantilever supporting the floating element) into the resonance frequency shift. Most popular shear stress sensors of this type are fiber-based Fabry-Perot interferometers (U.S. Pat. No. 6,426,796 B1).

The optical resonance methods are immune to electromagnetic radiation and can be realized in a size that is not larger than MEMS shear stress sensors described above. The fiber-based Fabry-Perot sensors, however, require a delicate mechanical alignment of the resonator (for example, rotational motion of the floating element may cause significant loss of the resonant signal quality). Another problem is the need for the Fabry-Perot resonator to be optically clean, a condition that is difficult to sustain in many applications.

The most important drawback of all known direct shear stress measurement methods is the requirement of a sizeable gap between the floating element and the wall, to give room for the floating element to shift under the shear force. This gap needs to be greater than at least 100 micrometers for all the described methods, to measure up to two orders of magnitude in shear stress (with the exception of the fiber-based Fabry-Perot interferometry). Most liquids penetrate holes larger than approximately 1 micrometer. Therefore, in all existing direct measurement shear stress sensors, the liquid will make its way into the internal elements of the sensor and will fill the gap. This may cause the inner elements of the sensor to malfunction and may impede the motion of the floating element. The problem can be solved by inserting a material between the floating element and the wall or by covering the gap from the side of the flow with a flexible material, however, that decreases sensitivity of the sensor and may be unsuitable for chemically active flows.

The drawback of the direct method is overcome in the approach that is commonly known as "whispering gallery modes" (WGM) optical measurement technology. Like the Fabry-Perot interferometry method, the WGM technology is based on observing changes in the spectrum of a resonator that is subjected to the external force. Instead of using an open resonator, as it is done in the Fabry-Perot interferometry, WGM employs dielectric micro-resonators (such as a glass sphere) with light captured inside. A minute change in the size, shape or refraction index of the micro-resonator alters the spectrum of the micro-resonator that manifests itself as a shift in its resonant frequency, a change in the magnitude for a particular resonance or in emergence of additional resonances in the spectrum. The micro-resonator spectrum can be measured, for example, by using a tunable laser and an optical detector. Usually, the shifts of the resonances are most practical to measure. Therefore, the discussion below is restricted to measuring the resonance shifts. The other features of the WGM spectra could also be employed in the method.

The optical resonances, or "whispering gallery modes" (WGM), are extremely narrow. Thus very small shifts of WGMs can be detected, which may be used for the precise measurements of the force causing the shifts (M. Kozhevnikov, T. Ioppolo, V. Stepaniuk, V. Sheverev and V. Otugen, "Optical Force Sensor Based on Whispering Gallery Mode Resonators," AIAA-2006-649, 44th AIAA Aerospace Sciences Meeting and Exhibit, Reno, Nev., Jan. 9-12, 2006). It has been shown that a change of a micro-sphere diameter as low as 0.01 nm can be detected by observing WGM shift (Ilchenko, V. S. et. al., "Strain-tunable high-Q optical microsphere resonator,' Optics Communications, 1998. 145(1-6): p. 86-90). That provides an opportunity for designing a floating element shear-stress sensor with an extremely narrow gap between the floating element and sensor wall. For example, for a gap of 100 nm that is not penetratable by any liquid, three orders of magnitude for the force can be measured.

A design for a shear stress sensor based on optical micro-resonators was proposed by Otugen & Sheverev (V. Otugen, V. Sheverev, U.S. patent application Ser. No. 11/926,793 (November 2007, see also M. Kozhevnikov, T. Ioppolo, V. Stepaniuk, V. Sheverev and V. Otugen, "Optical Force Sensor Based on Whispering Gallery Mode Resonators," AIAA-2006-649, 44th AIAA Aerospace Sciences Meeting and Exhibit, Reno, Nev., Jan. 9-12, 2006). In this design, the micro-resonator is placed between a movable floating element and the wall of the sensor, so that the micro-resonator effectively serves as a floating element support. Such an arrangement leads to the increased sensitivity of the sensor to the force acting normal to the surface of the floating element. This force may shift the floating element in the direction normal to the flow and change the position of the micro-resonator relative to the optical waveguide. The efficiency of the coupling will be affected which may lead to the WGM resonance shift caused by a normal force rather than shear force and, thus, to a false reading of the shear stress measurement.

SUMMARY OF THE INVENTION

A shear stress sensor for measuring the shear force of a flowing fluid, constructed in accordance with the present invention, includes a base element adapted for placement in a wall along which a fluid flows and a floating member for sensing a shear force of the fluid flowing along the wall. This shear stress sensor also includes a micro-resonator that changes in shape and refractive index in response to a force applied to the micro-resonator that changes the resonant frequency of the micro-resonator, whereby the spectrum of wavelengths of light introduced to the micro-resonator shifts. Also included in this shear stress sensor are support means; positioned between the floating member and the micro-resonator, for mounting the floating member to the base element to be flush with the wall and transmitting a force sensed by the floating member to the micro-resonator to change the resonant frequency of the micro-resonator. This shear stress sensor further includes optical carrier means for introducing light having a spectrum of wavelengths to the micro-resonator and providing an indication of a shift in the spectrum of wavelengths of the light caused by a change in the resonant frequency of the micro-resonator.

DETAILED DESCRIPTION OF THE INVENTION

Figure 1A:
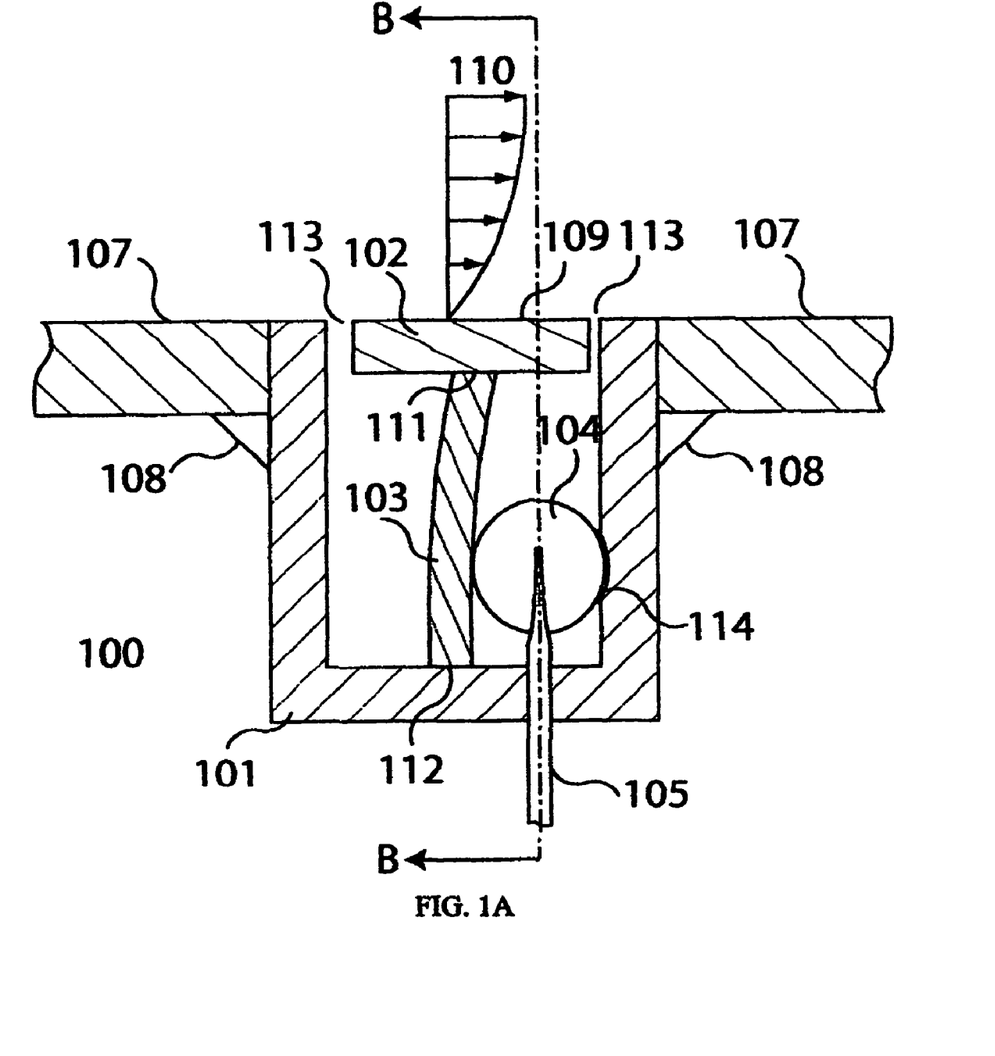
FIG. 1A is a sectional side view of a first embodiment of a shear stress sensor constructed in accordance with the present invention.
Figure 1B:
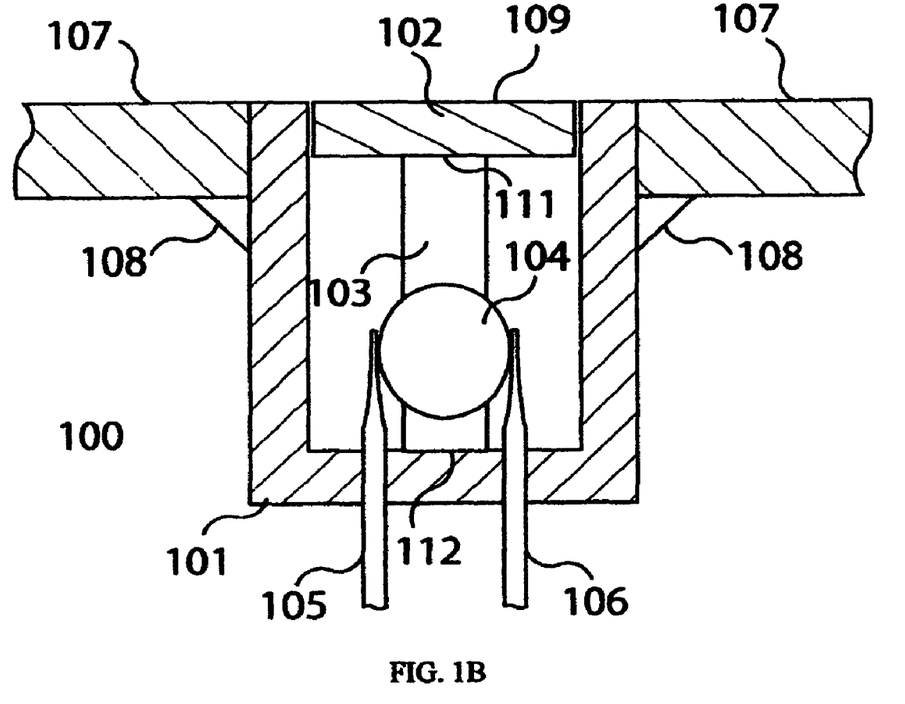
FIG. 1B is a sectional front view of the first embedment of a shear stress sensor constructed in accordance with the present invention taken along line B-B of FIG. 1A.

Referring to FIGS. 1A and 1B, a shear stress sensor 100, constructed in accordance with the present invention, includes a base element 101, a floating member 102, support means in the form of a lever member 103, a micro-resonator 104, and optical carrier means in the form of an input optical carrier 105 and an output optical carrier 106. Sensor 100 may be secured to a wall 107 by mechanical or chemical means 108. Surface 109 of floating element 102 is mounted flush with the test section of wall 107 and the floating element can move a short distance (typically 0.1 micrometers) along the flow direction represented by arrows 110. Lever member 103 is firmly attached at a first upper end 111 to floating member 102 and at a second lower end 112 to base element 101 in a manner that prevents vertical motion of the floating member. Unwanted vertical movement of floating member 102 is excluded because lever member 103 serves as a support member for the floating member and transfers shear force to micro-resonator 104.

A shear force, applied to floating member 102, is amplified by lever member 103 as the lever member squeezes micro-resonator 104, which is located between lever member 103 and base element 101. The amplified force on micro-resonator 104 increases minimal detectable shear stress, effectively increasing the sensitivity of the sensor. The closer micro-resonator 104 is to the lower end 112 of lever member 103, the higher the force amplification, and, therefore, the higher sensitivity. Depending on the application, the distance between micro-resonator 104 and the lower end 112 of lever member 103 may be adjusted based on the sensitivity and measurement dynamic range requirements of the application. The inside wall of base element 101 can be formed with an indentation 114 to hold micro-resonator 104 in place and prevent its movement.

Light from a tunable narrowband source, such as a laser, passes through input optical carrier 105 and is coupled into micro-resonator 104. Light from micro-resonator 104 is collected by output optical carrier 106 and transmitted to an optical detector. A spectrum containing WGMs is recorded by ramping the wavelength of the laser and recording the temporal dependence of the detector output. The change in the shape and the refractive index of micro-resonator 104, caused by being squeezed between lever member 103 and base element 101, alters the resonant frequency of the micro resonator that is observed in the spectrum as a shift in WGMs. This shift is related to the shear stress using the known theoretical model or a calibration curve.

Floating member 102 may be made of the same or different material as the test section wall 107. Surface 109 of floating member 102 may be modified, for example by being polished or roughed, covered with other material or be bare. The shape of the surface may repeat the shape of the surrounding wall and be plane, convex, concave or another.

The size of gaps 113 between floating member 102 and the inside walls of base element 101 can be less than one micrometer because the maximum deformation of micro-resonator 104 can be of the order of a few nanometers. Such small gaps will not disturb the flow and prevent fluid propagation into the sensor, therefore, eliminating the need to cover gaps 113 with flexible material.

Lever member 103 may have a rectangular or other cross-section. The dimensions of lever member 103 may be optimized for the particular application. Lever member 103 can be made of different materials with a different modulus of elasticity to obtain an optimal response for the fluid flows with different expected shear stresses, while providing the necessary support for floating element 102 to exclude unwanted vertical movement of the floating member transverse to the flowing fluid that passes over the floating member.

Micro-resonator 104 may have various geometries, for example spherical, disk, elliptical and other and may be made of glass, plastic or other material transparent to the interrogating light.

Although a single optical carrier (fiber or waveguide) can be used to couple the interrogating light into micro-resonator 104 and to deliver the transmitted light to an optical detector to provide an indication of a shift in the spectrum of wavelengths of the light caused by a change in the resonant frequency of the micro-resonator, in many applications of the present invention employing separate optical carriers for introducing light to the micro-resonator and collecting light from the micro-resonator will be preferred. This is shown in FIGS. 1A and 1B. Light is delivered to micro-resonator 104 by a first optical carrier 105 and collected by a second optical carrier 106. In the FIGS. 1A and 1B embodiment of the present invention, the input optical carrier 105 and the output optical carrier 106 are coupled to micro-resonator 104 at different places. Coupling may be facilitated by placing, in the vicinity of micro-resonator 104, a stretched fiber, an angle polished fiber, a prism, or other means. An on-chip system with an etched micro-resonator and optical waveguides, for example, can be employed. The above elements can be manufactured using MEMs technology.

The general appearance of the WGM spectrum, when only one optical carrier is used, is typical of an absorption spectrum. The general appearance of the WGM spectrum, when separate optical carriers are used to introduce light to and collect light from the micro-resonator, is typical of an emission spectrum. Because the coupling efficiency is different for different micro-resonator modes, the depths of the valleys or the heights of the peaks of the WGM spectrum also are different. To accurately find the position of a valley or a peak, the magnitude of the valley or the peak should be larger than the noise level in the detection system which is usually determined by the amplification factor. When one optical carrier is used, the amplification factor is fixed because it is defined by the light source intensity. When two optical carriers are used, the amplification factor is determined by the magnitude of the highest peak of the WGM spectrum and can be 100-1000 times higher, so that the signal-to-noise ratio also is higher. As a result, weaker WGM resonances can be observed and their position can be determined more accurately which leads to improvement of the sensor sensitivity.

Another benefit of employing separate optical carriers for introducing light to and collecting light from the micro-resonator is that, in general, when a single optical carrier is used, the physical size of the sensor is likely to be larger than desired for the particular application. A single optical carrier configuration requires bending the optical carrier inside the sensor housing to form a loop with a radius large enough to avoid significant loss of light. When separate optical carriers are used, a return loop is not needed, so that the sensor physical size is smaller.

Figure 2:
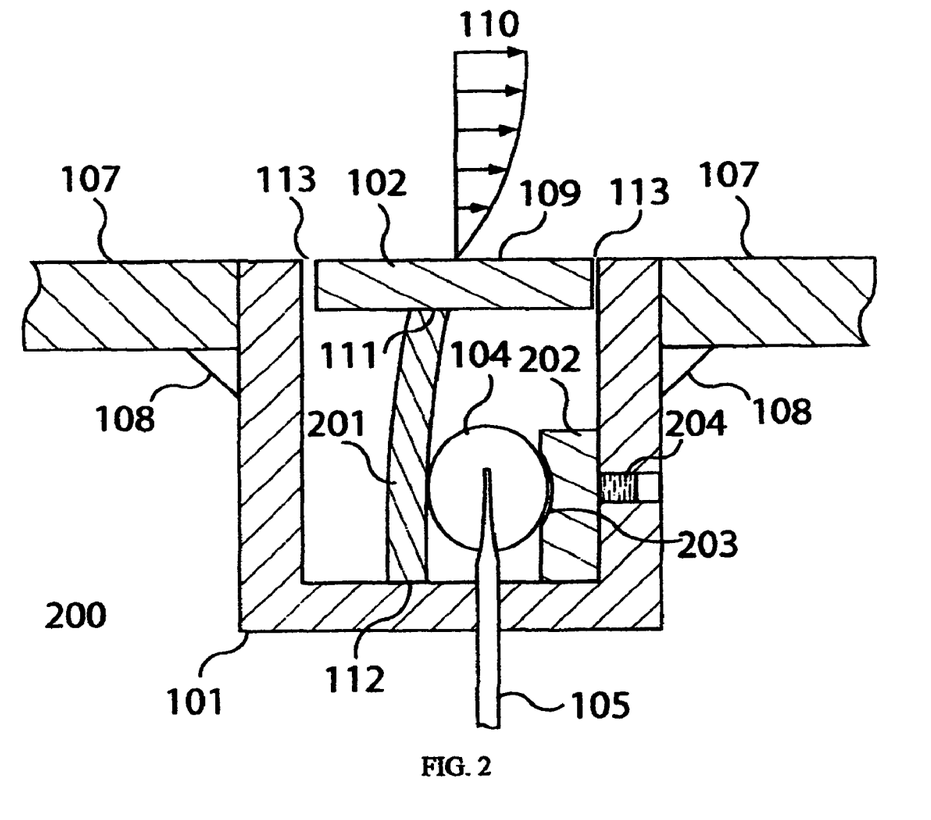
FIG. 2 is a sectional side view of a second embodiment of a shear stress sensor constructed in accordance with the present invention.

Micro-resonator 104 may be placed between lever member 103 and the inside wall of base element 101, as shown in FIG. 1A, or between a lever member 201 and a micro-resonator holder member 202, as shown in the FIG. 2, which illustrates a second embodiment of shear stress sensor 200 constructed in accordance with the present invention. Components in FIG. 2, corresponding to components in FIGS. 1A and 1B, have been given the same reference numerals used in FIGS. 1A and 1B. Micro-resonator holder member 202 can be formed with an indentation 203 to hold micro-resonator 104 in place and prevent its movement. The position of micro-resonator 104 may be adjusted to initially stress preload (compress) the micro-resonator by means of a preload component, such as a setscrew 204, that moves micro-resonator holder 202 away from or back to the wall of base element 101.

Figure 3:
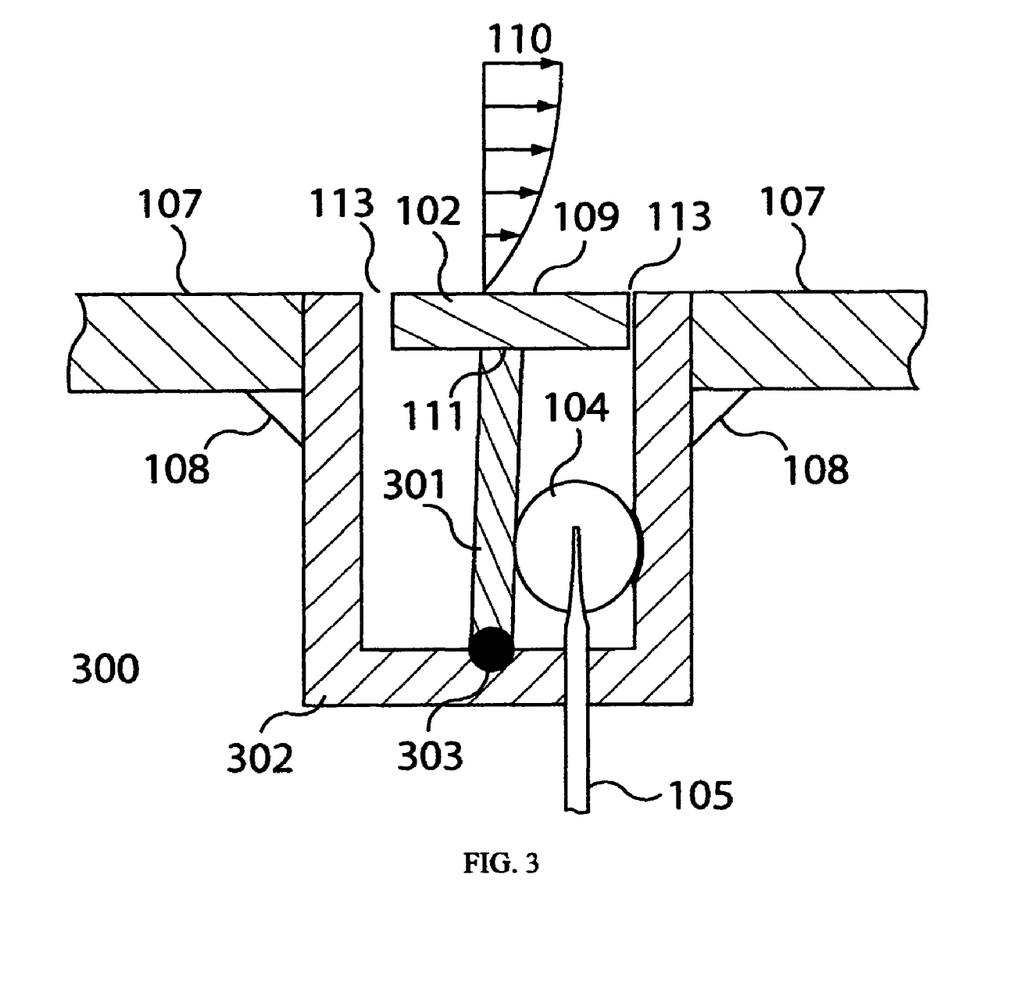
FIG. 3 is a sectional side view of a third embedment of a shear stress sensor constructed in accordance with the present invention.

A third embodiment of a shear stress sensor 300, constructed in accordance with the present invention, is illustrated in FIG. 3, in which components corresponding to components in FIGS. 1A and 1B have been given the same reference numerals used in FIGS. 1A and 1B. In this third embodiment, a lever member 301 is mounted for pivotal movement in a base element 302 to increase sensitivity of the sensor. Lever member 301 can be mounted to base element 302 by means of a bearing 303.

Figure 4:
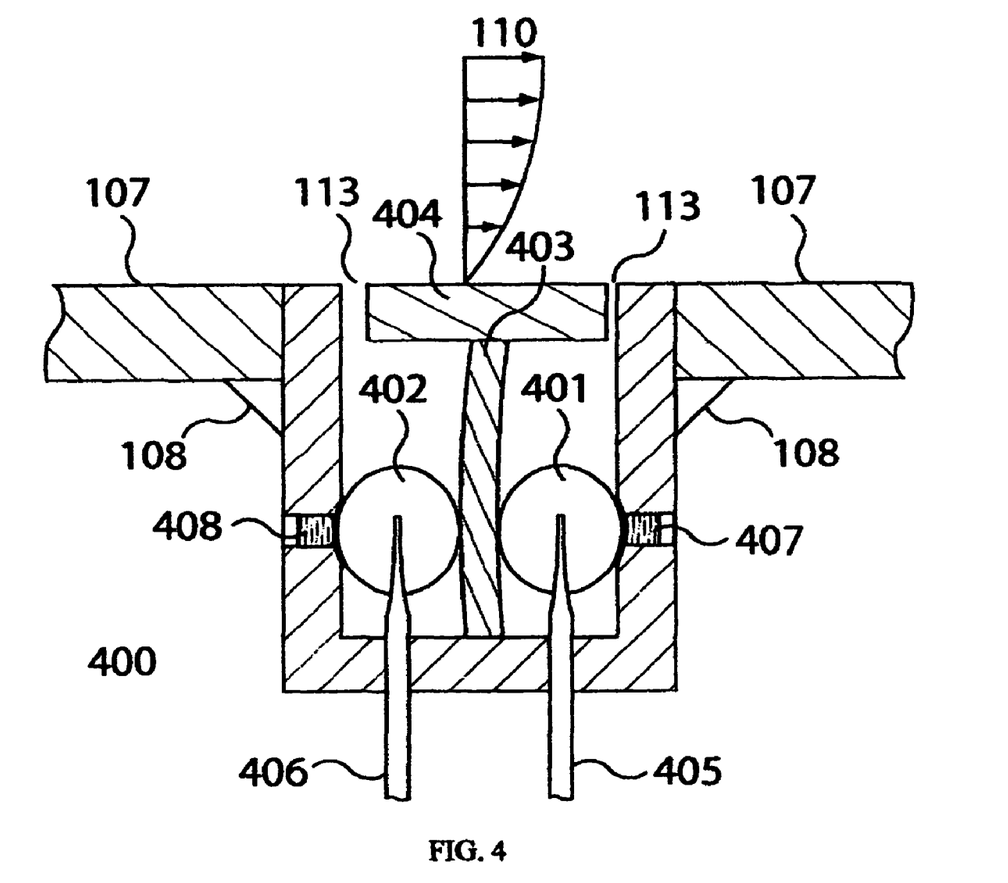
FIG. 4 is a sectional side view of a fourth embodiment of a shear stress sensor constructed in accordance with the present invention.

Referring to FIG. 4, in which components corresponding to components in FIGS. 1A and 1B have been given the same reference numerals used in FIGS. 1A and 1B, a shear-stress sensor 400, constructed in accordance with the present invention, has two micro-resonators 401 and 402. One micro-resonator is placed on each side of a lever member 403 that supports a floating member 404. Interrogating light is introduced to micro-resonators 401 and 402 through input optical carriers 405 and 406, respectively, and is collected from the micro-resonators by two output optical carriers (not shown) individually associated with the micro-resonators and the input optical carriers in a manner similar to the FIG. 1B embodiment of the present invention but which has only one micro-resonator.

When shear force is applied to floating member 404, the shear force is transferred to micro-resonators 401 and 402 by lever member 403. If micro-resonators 401 and 402 are preloaded, for example by preload components 407 and 408, respectively, application of the force to the translation member, namely lever member 403, leads to the squeezing of one micro-resonator (e.g., micro-resonator 401) and the decompressing of the other micro-resonator (e.g., micro-resonator 402). WGM spectra from the two resonators will shift in opposite senses due to a change in shape and refractive index of micro-resonator 401 in a first sense and a change in shape and refractive index in a second and opposite sense of micro-resonator 402. Other factors, for example a change of the sensor temperature, may lead to the shift of the WGM spectra in the same direction. Therefore, utilizing two micro-resonator sensors, as illustrated in FIG. 4, makes possible compensation of environmental influence on the shear stress measurements.

Figure 5:
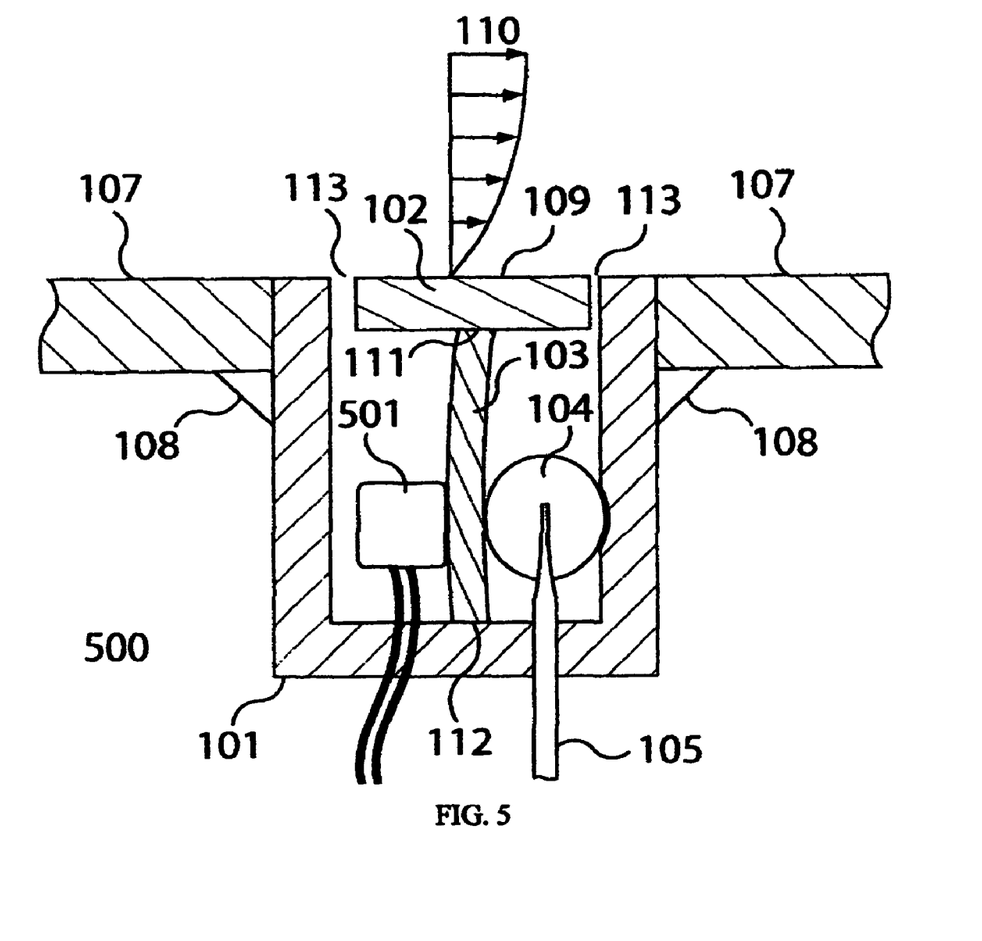
FIG. 5 is a sectional side view of a fifth embodiment of a shear stress sensor constructed in accordance with the present invention.

FIG. 5 illustrates a fifth embodiment of a shear stress sensor constructed in accordance with the present invention. The FIG. 5 shear stress sensor is similar to the shear stress sensor of FIGS. 1A and 1B, but adds an environmental sensor 501, for example a thermocouple or a thermistor, that is positioned in proximity to micro-resonator 104 to sense temperature change. Environmental sensor 501 serves in compensating for spectrum shift in the micro-resonator due to the influence of an environmental factor, such as temperature. If the dependence of the spectrum shift versus change in the environmental condition, such as temperature, is known, for example from a theoretical model or from calibration measurements, the measurement results can be adjusted according to the environmental sensor readings.

A second micro-resonator may serve as a reference for compensating for spectrum shift in micro-resonator 104 due to the influence of an environmental factor. This second micro-resonator would be installed in the shear stress sensor in such a way that it is not acted on by a component, such as lever 103, that reacts to movement of floating member 102, so that only environmental factors, such as sensor temperature change, will affect a spectrum shift of the second micro-resonator. The spectrum shift of micro-resonator 104 can be recalculated taking into account the spectrum shift of the second micro-resonator compensating for the environmental influence.

Figure 6:
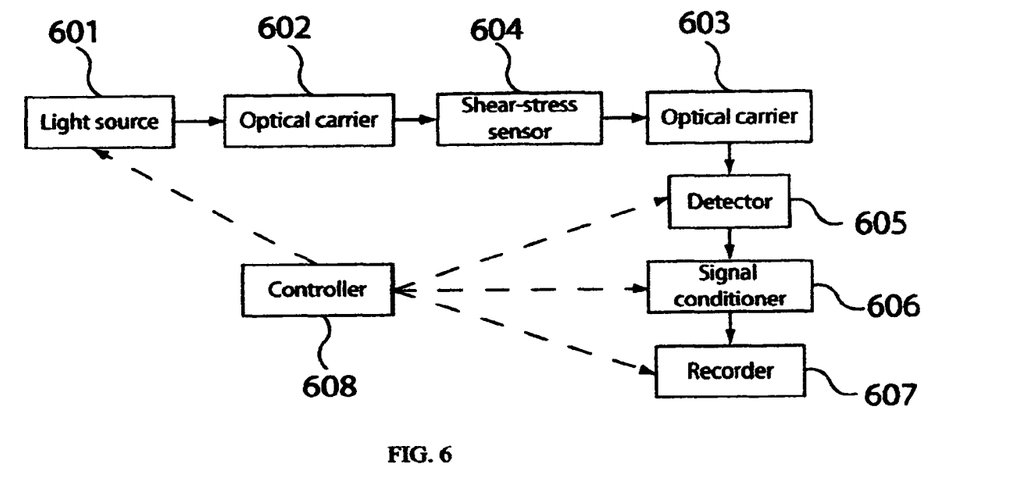
FIG. 6 is a schematic diagram of a system for measuring shear stress based on a shift of optical resonances of a micro-resonator constructed in accordance with the present invention.

FIG. 6 illustrates a system for shear stress measurement constructed in accordance with the present invention. This system includes a narrowband tunable light source 601, an input optical carrier 602, an output optical carrier 603, a shear stress sensor 604, a detector 605, a signal conditioner 606, a data recorder 607, and a controller 608.

Light from narrowband tunable source 601, for example a tunable diode laser, is directed through input optical carrier 602, for example an optical fiber, to a shear stress sensor 604 in accordance with the present invention. The light wavelength is ramped between preset limits. Inside shear stress sensor 604, light is coupled into one or more micro-resonator (s). Shear stress sensor 604 is installed flush with a test wall in such a way that a surface of the floating element of the shear stress sensor is exposed to the fluid flow and the shear force that is acting on it. Shear force, transferred to the micro-resonator(s) through the lever member, changes the shape and the index of refraction of the micro-resonator(s) which leads to a shift of the WGM resonances. Light emanating from the micro-resonator(s) is collected by an output optical carrier 603 and transmitted to detector 605, for example a photodiode, that produces an electrical signal, the strength of which is related to the light intensity. The electrical signal is conditioned in signal conditioner 606, for example a photodiode amplifier, and recorded and stored by recorder 607, for example a computer with a data acquisition card. The WGM spectrum is recorded when the light wavelength is swept from the preset minimum to the preset maximum. Operation of light source 601, detector 605, signal conditioner 606 and recorder 607 is synchronized and controlled by a controller 608, for example a computer with appropriate software. The shift of the resonances in the WGM spectrum can be determined by comparing the obtained WGM spectrum with a WGM spectrum recorded before the force was applied to the sensor. Resonance shift then can be related to the shear stress using a calibration curve or theoretical formula.

Figure 7:
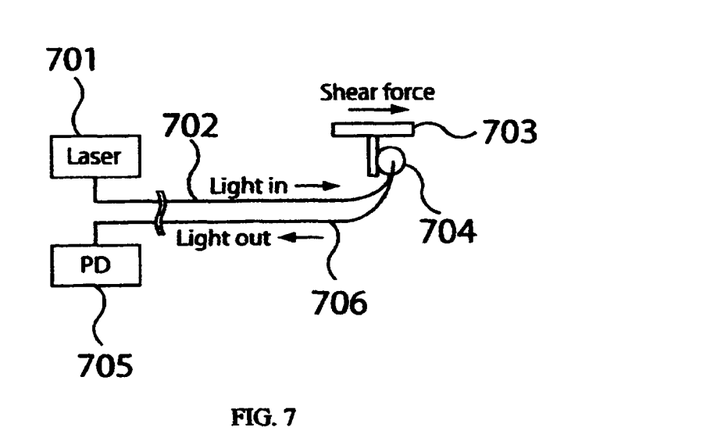
FIG. 7 is a schematic diagram of the components of an optical circuit for measuring shear stress based on a shift of optical resonances of a micro-resonator constructed in accordance with the present invention.

An exemplary optical circuit for shear stress measurement, in accordance with the present invention, is shown in FIG. 7. Light from a diode laser 701 is transmitted through an optical fiber 702 to a wall shear stress sensor 703 and coupled to a micro-resonator 704. Light emanating from micro-resonator 704 is directed to a photodiode 705 through an optical fiber 706.

Figure 8:
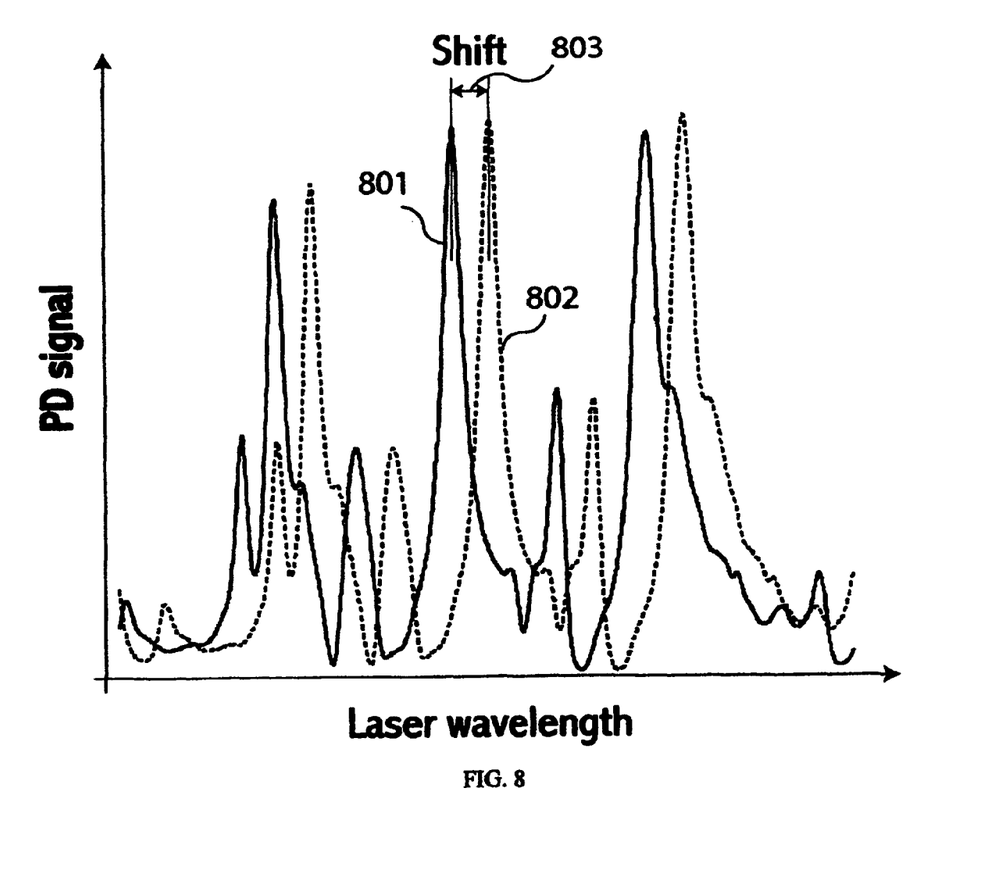
FIG. 8 illustrates a shift of optical resonances of a micro-resonator as a force is applied to the micro-resonator.
Figure 9:
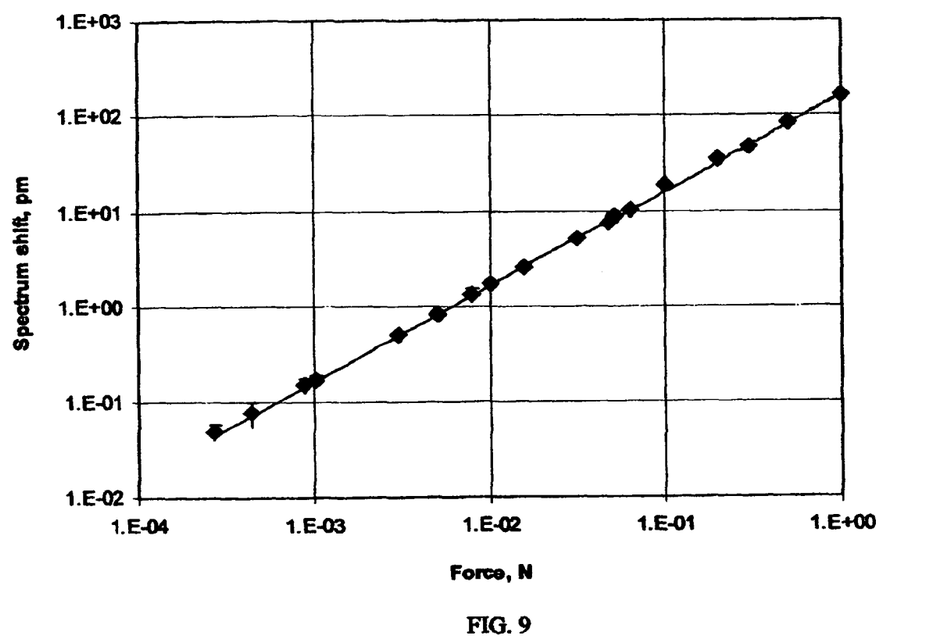
FIG. 9 is a graph that presents an exemplary measurement of the force vs. shift of the optical resonances of a micro-resonator.

Two examples of measured WGM spectra are presented in FIG. 8. Spectrum 801 represents no shear force being applied to the floating member of the sensor and spectrum 802 represents shear force being applied to the floating member of the sensor. Shear force transferred by the lever member to the micro-resonator changes the shape and index of refraction of the micro-resonator, which leads to the WGM spectrum shift 803. Shear stress is determined by measuring the magnitude of the spectrum shift and using a sensor calibration curve. An example of a calibration curve is given in FIG. 9.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A shear stress sensor for measuring the shear force of a flowing fluid comprising:
   a base element adapted for placement in a wall along which a fluid flows;

a floating member for sensing a shear force of the fluid flowing along the wall;

a micro-resonator that changes in shape and refractive index in response to a force applied to said micro-resonator that changes the resonant frequency of said micro-resonator, whereby the spectrum of wavelengths of light introduced to said micro-resonator shifts;

support means, positioned between said floating member and said micro-resonator, for:
(a) mounting said floating member to said base element to be flush with the wall, and
(b) transmitting a force sensed by said floating member to said micro-resonator to change the resonant frequency of said micro-resonator; and optical carrier means for:
(a) introducing light having a spectrum of wavelengths to said micro-resonator, and
(b) providing an indication of a shift in the spectrum of wavelengths of the light caused by a change in the resonant frequency of said micro-resonator.

2. A shear stress sensor according to claim 1 wherein said support means is a lever having a first end attached to said floating member and a second end attached to said base element.

3. A shear stress sensor according to claim 2 further including a bearing by which said second end of said of lever is attached to said base element for pivotal movement of said lever.

4. A shear stress sensor according to claim 1 further including means for sensing an environmental factor in the proximity of said micro-resonator to compensate for spectrum shift in said micro-resonator due to the influence of the environmental factor.

5. A shear stress sensor according to claim 1 further including pre-load means for adjusting the position of said micro-resonator.

6. A shear stress sensor according to claim 2 wherein said optical carrier means include:
(a) a first optical carrier for introducing to said micro-resonator light having a first spectrum of wavelengths, and
(b) a second optical carrier for collecting from said micro-resonator light having a second spectrum of wavelengths.

7. A shear stress sensor for measuring the shear force of a flowing fluid comprising:
a base element adapted for placement in a wall along which a fluid flows;
a floating member for sensing a shear force of the fluid flowing along the wall;
a first micro-resonator that changes in shape and refractive index in response to a force applied to said first micro-resonator that changes the resonant frequency of said first micro-resonator, whereby the spectrum of wavelengths of light introduced to said first micro-resonator shifts;
a second micro-resonator that changes in shape and refractive index in response to a force applied to said second micro-resonator that changes the resonant frequency of said second micro-resonator, whereby the spectrum of wavelengths of light introduced to said second micro-resonator shifts;
support means, positioned:
(a) between said floating member and said first micro-resonator, and,
(b) between said floating member and said second micro-resonator,
for:
(a) mounting said floating member to said base element to be flush with the wall, and
(b) transmitting a force sensed by said floating member to:
(1) said first micro-resonator to change the resonant frequency of said first micro-resonator, and
(2) said second micro-resonator to change the resonant frequency of said second micro-resonator; and optical carrier means for:
(a) introducing light having a spectrum of wavelengths to said first micro-resonator and to said second micro-resonator, and
(b) providing indications of shifts in the spectrums of wavelengths of the light caused by changes in the resonant frequencies of said first micro-resonator and said second micro-resonator.

8. A shear stress sensor according to claim 7 wherein said support means is a lever having a first end attached to said floating member and a second end attached to said base element.

9. A shear stress sensor according to claim 8 further including a bearing by which said second end of said of lever is attached to said base element for pivotal movement of said lever.

10. A shear stress sensor according to claim 7 further including pre-load means for adjusting the positions of said first micro-resonator and said second micro-resonator.

11. A shear stress sensor according to claim 8 wherein said optical carrier means include:
(a) a first optical carrier for introducing light having a first spectrum of wavelengths to said first micro-resonator and a second optical carrier for collecting light from said first micro-resonator having a second spectrum of wavelengths, and
(b) a third optical carrier for introducing light having a first spectrum of wavelengths to said second micro-resonator and a fourth optical carrier for collecting light from said second micro-resonator having a second spectrum of wavelengths.

12. A system for measuring shear stress comprising:
a shear stress sensor including:
(a) a base element adapted for placement in a wall along which a fluid flows,
(b) a floating member for sensing a shear force of the fluid flowing along the wall,
(c) a micro-resonator that changes in shape and refractive index in response to a force applied to said micro-resonator that changes the resonant frequency of said micro-resonator, whereby the spectrum of wavelengths of light introduced to said micro-resonator shifts,
(d) support means, positioned between said floating member and said micro-resonator, for:
(1) mounting said floating member to said base element to be flush with the wall, and
(2) transmitting a force sensed by said floating member to said micro-resonator to change the resonant frequency of said micro-resonator, and
(e) optical carrier means for:
(1) introducing light having a spectrum of wavelengths to said micro-resonator, and
(2) providing an indication of a shift in the spectrum of wavelengths of the light caused by a change in the resonant frequency of said micro-resonator;

a light source for supplying light having a ramped wavelength to said optical carrier means;

a detector for receiving light from said optical carrier means for producing an electrical signal representative of the intensity of the light received from said optical carrier means; and means for recording the intensity of the light received from said optical carrier means.

13. A shear stress sensor according to claim 2 further including means for sensing an environmental factor in the proximity of said micro-resonator to compensate for spectrum shift in said micro-resonator due to the influence of the environmental factor.

14. A shear stress sensor according to claim 2 further including pre-load means for adjusting the position of said micro-resonator.

15. A shear stress sensor according to claim 8 further including pre-load means for adjusting the positions of said first micro-resonator and said second micro-resonator.

* * * * *